United States Patent [19]

Fuchs

[11] 4,017,529
[45] Apr. 12, 1977

[54] HERBICIDAL ALLOPHANIMIDATES

[75] Inventor: Julius Jakob Fuchs, Wilmington, Del.

[73] Assignee: E. I. Du Pont de Nemours and Company, Wilmington, Del.

[22] Filed: Feb. 27, 1975

[21] Appl. No.: 553,628

Related U.S. Application Data

[60] Division of Ser. No. 268,768, July 3, 1972, Pat. No. 3,879,190, which is a continuation-in-part of Ser. No. 256,254, May 24, 1972, abandoned, which is a continuation-in-part of Ser. No. 181,203, Sept. 16, 1971, abandoned.

[52] U.S. Cl. .............................. 260/453 R; 71/100; 71/105; 260/239 E; 260/239 B; 260/293.88; 260/293.89; 260/293.9; 260/326.8; 260/326.9; 260/465.2; 260/465 B; 260/471 C; 260/475 SC; 260/481 C; 260/482 B
[51] Int. Cl.² .............. C07C 119/18; C07C 119/20
[58] Field of Search ..................... 260/453 R; 71/98

[56] References Cited

UNITED STATES PATENTS

| | | | |
|---|---|---|---|
| 2,780,535 | 2/1957 | Snyder | 71/98 |
| 3,424,723 | 1/1969 | Yates et al. | 71/98 |
| 3,488,355 | 1/1970 | Levy | 260/453 R |

FOREIGN PATENTS OR APPLICATIONS

| | | | |
|---|---|---|---|
| 4,118,958 | 11/1966 | Japan | 71/99 |
| 4,316,470 | 7/1968 | Japan | 71/99 |

OTHER PUBLICATIONS

Sonn, "Biuret and Triuret from Urea," (1942) CA 37 p. 6281 (1943).
Najer et al., "Action of Oxabyl Chloride etc.," (1959).

*Primary Examiner*—Glennon H. Hollrah

[57] ABSTRACT

Herbicidal allophanimidic acid esters of the formula:

$$R_1\phantom{x}X_1\phantom{xxxx}R_3\phantom{x}X_3\phantom{xxx}R_4$$
$$\phantom{xx}\searrow\phantom{x}\|\phantom{xxxxx}|\phantom{xx}\|\phantom{xxx}\diagup$$
$$\phantom{xxxx}N-C-N=C-N-C-N$$
$$\diagup\phantom{xxxxxxxx}|\phantom{xxxxxxxxx}\diagdown$$
$$R_2\phantom{xxxxxx}X_2-R_6\phantom{xxxxx}R_5$$

where
$R_1$, $R_2$, $R_4$ and $R_5$ are selected from hydrogen and certain organic radicals, at least one of them being an organic radical;
$R_3$ is selected from hydrogen and certain organic radicals;
$R_6$ is selected from certain organic radicals; and
$X_1$, $X_2$, and $X_3$ are selected from oxygen and sulfur; and salts of the above compounds in which $R_3$ is hydrogen.

Preparation of the compounds by carbamoylation of $$R_1\phantom{x}X_1$$
$$\phantom{xx}\searrow\phantom{x}\|$$
$$\phantom{xxxx}N-C-N=C-NHR_3$$
$$\diagup\phantom{xxxxxxxx}|$$
$$R_2\phantom{xxxxxx}X_2-R_6$$

or by reaction of ammonia or an amine with $$R_1\phantom{x}X_1\phantom{xxxx}R_3\phantom{x}X_3$$
$$\phantom{xx}\searrow\phantom{x}\|\phantom{xxxxx}|\phantom{xx}\|$$
$$\phantom{xxxx}N-C-N=C-N-C-Y$$
$$\diagup\phantom{xxxxxxxx}|$$
$$R_2\phantom{xxxxxx}X_2-R_6$$

where Y is —SCH$_3$, —Cl, or $$-N\diagdown\!\!\!=\!\!\!\diagup$$
$$\phantom{xx}\diagup\!\!\!=\!\!\!\diagdown_N$$

An exemplary compound: methyl N-dimethylcarbamoyl-4-tert-butylthioallophanimidate.

12 Claims, No Drawings

HERBICIDAL ALLOPHANIMIDATES

CROSS REFERENCE TO RELATED APPLICATIONS

This is a division of Ser. No. 268,768, filed July 3, 1972 now U.S. Pat. No. 3,879,190, which is a continuation-in-part of Ser. No. 256,254, filed May 24, 1972, now abandoned, which is a continuation-in-part of Ser. No. 181,203, filed Sept. 16, 1971, now abandoned.

BACKGROUND OF THE INVENTION

U.S. Pat. No. 3,530,220, issued Sept. 22, 1970, to James B. Buchanan, discloses a class of 1-carbamoyl-N-(substituted carbamoyloxy)thioformimidates of the general formula

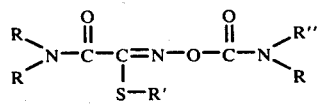

where the R's represent hydrogen or certain organic radicals and R' and R'' represent certain organic radicals. The compounds are insecticides, acaricides, and nematocides. The patent discloses preparation of the compounds from intermediate 1-carbamoyl-N-hydroxythioformimidates of the general formula

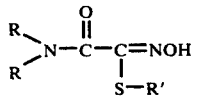

The present invention resulted from efforts to discover new biologically active compounds which could be prepared from these intermediates.

SUMMARY OF THE INVENTION

This invention is a class of novel herbicidally active compounds of the formula:

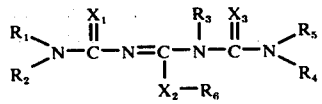

wherein:
$R_1$, $R_2$, $R_4$ and $R_5$ are each independently selected from the group consisting of hydrogen; alkyl of 1 through 8 carbon atoms; alkenyl of 3 through 4 carbon atoms; cycloalkyl of 3 through 8 carbon atoms; cycloalkenyl of 5 through 8 carbon atoms; cycloalkylalkyl of 4 through 10 carbon atoms; bicycloalkyl of 7 through 10 carbon atoms; arylalkyl of 5 through 9 carbon atoms; alkynyl of 3 through 4 carbon atoms; methoxy; phenyl; the above alkyl and alkenyl groups substituted with 1 through 3 chlorines, bromine, iodine, 1 through 7 fluorines, methoxy, ethoxy, methylthio, ethylthio, cyano, methoxycarbonyl, ethoxycarbonyl, or acetyl; the above cycloalkyl nd bicycloalkyl groups substituted with 1 through 3 chlorines, bromine, 1 or 2 methyls, or alkyl of 2 through 4 carbon atoms; phenyl substituted with 1 or 2 chlorines, 1 or 2 bromines, fluorine, nitro, cyano, alkyl of 1 through 4 carbon atoms, methoxy, or trifluoromethyl; and the above arylalkyl groups substituted with 1 chlorine or 1 methyl;

$R_1$ and $R_2$ when taken together and $R_4$ and $R_5$ when taken together are $-(CH_2)_2-O-(CH_2)_2-$ or $-(CH_2)_n-$ where $n$ is 2 through 6;

$R_3$ is hydrogen; alkyl of 1 through 4 carbon atoms; alkynyl of 3 through 4 carbon atoms; or alkenyl of 3 through 4 carbon atoms;

$R_6$ is alkyl of 1 through 8 carbon atoms; cycloalkyl of 5 through 8 carbon atoms; alkenyl of 3 through 8 carbon atoms; phenyl; or benzyl; and $X_1$, $X_2$, and $X_3$ are each independently selected from oxygen and sulfur;

provided that:
a. at least one of $R_1$, $R_2$, $R_4$ and $R_5$ is other than hydrogen;
b. no more than one of $R_1$, $R_2$, $R_4$ and $R_5$ is phenyl, substituted phenyl; arylalkyl or substituted arylalkyl;
c. the total number of carbon atoms in $R_1$ and $R_2$ does not exceed 10;
d. the total number of carbon atoms in $R_4$ and $R_5$ does not exceed 10;
e. $R_1$ and $R_2$ are not both methoxy;
f. $R_4$ and $R_5$ are not both methoxy;
g. when one of $R_1$, $R_2$, $R_4$ and $R_5$ is methoxycarbonylmethyl or ethoxycarbonylmethyl and $R_3$ is hydrogen then only one of the other $R_1$, $R_2$, $R_4$ and $R_5$ can be other than hydrogen;
h. when $R_6$ is normal alkyl of 3 through 8 carbon atoms, cycloalkyl of 6 through 8 carbon atoms and benzyl, and $R_3$ is hydrogen, and one of $R_1$, $R_2$, $R_4$ and $R_5$ is phenyl, then only one of the other $R_1$, $R_2$, $R_4$ and $R_5$ can be other than hydrogen; and
i. when one of $R_1$, $R_2$, $R_4$ and $R_5$ is 2,5-dichlorophenyl and $R_3$ is hydrogen, then only one of the other $R_1$, $R_2$, $R_4$ and $R_5$ can be other than hydrogen;

and salts of the above compounds in which $R_3$ is hydrogen.

The invention also includes herbicidal compositions containing the compounds as active ingredient, methods of controlling undesired vegetation by applying the compounds, methods of preparing the compounds, and certain intermediates (Compounds of formulae II, III and V below) useful in preparing the compounds.

DESCRIPTION OF THE INVENTION

Preferred Compounds

Preferred because of higher herbicidal activity and ease of synthesis are those compounds of formula I where
$R_1$ is hydrogen, alkyl of 1 through 6 carbon atoms, or alkenyl of 3 through 4 carbon atoms;
$R_2$ is alkyl of 1 through 4 carbon atoms or alkenyl of 3 through 4 carbon atoms, provided that the total number of carbon atoms in $R_1$ and $R_2$ does not exceed 8;
$R_3$ is hydrogen;
$R_4$ is alkyl of 1 through 6 carbon atoms, alkenyl of 3 through 4 carbon atoms or cycloalkyl of 5 through 6 carbon atoms;
$R_5$ is hydrogen, alkyl of 1 through 6 carbon atoms, cycloalky of 5 through 6 carbon atoms, benzyl, or alkenyl of 3 through 4 carbon atoms;
$R_6$ is methyl, ethyl, isopropyl or allyl;
$X_1$ and $X_3$ are oxygen; and $X_2$ is oxygen or sulfur.

Most preferred because of their higher activity are those compounds of formula I where
- $R_1$ is hydrogen or methyl;
- $R_2$ is alkyl of 1 through 4 carbon atoms;
- $R_3$ is hydrogen;
- $R_4$ is alkyl of 1 through 4 carbon atoms, allyl or cycloalkyl of 5 through 6 carbon atoms;
- $R_5$ is hydrogen;
- $R_6$ is methyl;
- $X_1$ and $X_3$ are oxygen; and
- $X_2$ is sulfur.

The compounds of formula I where $R_4$ is phenyl or substituted phenyl are preferred for some uses as they have exhibited selective herbicidal activity in crops such as corn and cotton.

Preferred compounds of formula I include:
methyl N-dimethylcarbamoyl-4-allylthioallophanimidate
methyl N-dimethylcarbamoyl-4-isopropylthioallophanimidate
methyl N-dimethylcarbamoyl-4-tert-butylthioallophanimidate
methyl N-dimethylcarbamoyl-4-cyclohexylthioallophanimidate
methyl N-isopropylcarbamoyl-4-isopropylthioallophanimidate
methyl N-tert-butylcarbamoyl-4-methylthioallophanimidate
methyl N-tert-butylcarbamoyl-4-tert-butylthioallophanimidate
methyl N-cyclohexylcarbamoyl-4-methylthioallophanimidate
methyl N-sec-butylcarbamoyl-4-sec-butylthioallophanimidate
methyl N-n-butylcarbamoyl-4-n-butylthioallophanimidate

Synthesis of the final products

Compounds of formula I can be prepared by either of the following two reactions:

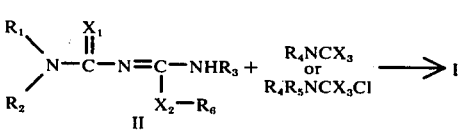

(A)

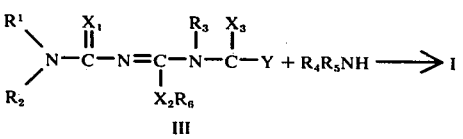

(B)

where Y is $-SCH_3$, $-Cl$, or $-N\diagup\!\!\!\diagdown\!\!\!\!N$ ; and $R_1$ through $R_6$ and $X_1$ through $X_3$ are as hereinbefore defined, except that: in the isocyanates and isothiocyanates ($R_4NCX_3$), $R_4$ is not methoxy; in the carbamoyl and thiocarbamoyl chlorides ($R_4R_5NCX_3Cl$), $R_4$ and $R_5$ are not both H; and $X_3$ in $R_4NCX_3$ is not sulfur when $X_2$ in the compound of formula II is sulfur.

Carbamylation reaction A is carried out in an inert organic solvent such as methylene chloride, acetone, ethyl acetate, benzene, $CCl_4$, $CH_2Cl_2$, or petroleum ether, at a temperature in the range of about $-30°$ to $100°$ C. A temperature in the range of about $0°$ to $100°$ C is usually used, and a temperature in the range of about $20°$ to $70°$ C is usually preferred. The optimum temperature in a given instance, of course, will depend upon the reactivity of the starting materials involved. When the carbamylating agent is $HNCX_3$, the reaction is carried out in a nonpolar solvent, and the reactant is conveniently generated in situ by reaction of an alkali metal cyanate or thiocyanate (e.g. NaCNO or NaNCS) and an acid (e.g. HCl or $CF_3COOH$). When the carbamylating agent is $R_4R_5NCX_3Cl$, the reaction is carried out in a nonpolar solvent in presence of an acid acceptor such as pyridine or triethylamine.

Reaction B is also carried out in an inert organic solvent, such as methanol, dimethylformamide (DMF), dimethylsulfoxide (DMSO), or acetone. Temperatures in the range of about $-10°$ to $100°$ C are suitable. A temperature in the range of about $0°-50°$ C is usually used, and ambient temperature is preferred.

Both reactions A and B can be carried out at reduced or elevated pressures. For example, pressures in the range of 0.1 to 3 atmospheres can be used, but atmospheric pressure is suitable in most cases, and is preferred.

The salts of those compounds of formula I where $R_3$ is H are prepared as follows:

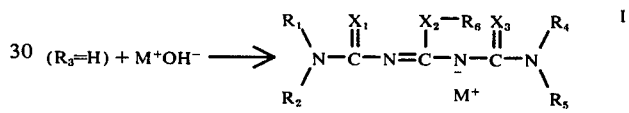

where $M^+$ is a cation such as $Li^+$, $Na^+$, $K^+$, $Cs^+$, $(Ca/2)^+$, $(Mg/2)^+$, or quaternary ammonium.

The reaction is run in water with optional water miscible solvents.

Alternatively, a salt exchange reaction can be used, as for example solution of the sodium salt in water followed by addition of a solution of calcium chloride to precipitate the less soluble calcium salt.

Synthesis of intermediates

Intermediates of formula II can be prepared in various ways, as illustrated by the following processes:

Process 1

All compounds of formula II wherein $X_1$ is oxygen can be made by the following two step process:

Step 1

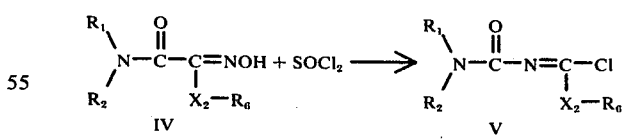

Step 2

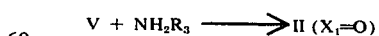

Step 1

The Beckmann rearrangement of the formhydroxamates and thioformhydroxamates of formula IV to the formimidoyl and thioformimidoyl chlorides of formula V can be carried out with $PCl_5$, $POCl_3$ or $SOCl_2$ in any inert solvent which will dissolve the reaction product, such as benzene, toluene, $CCl_4$, $CHCl_3$ or $CH_2Cl_2$. Methylene chloride and thionyl chloride are preferred because of gaseous reaction products being formed from the acid chloride, and because of the high volatility of the solvent. The temperature of the reaction is not critical. Experience has shown that a reaction temperature below room temperature gives increased yields of the formimidoyl chloride; this the preferred range is 0°–20° C. The thioformhydroxamates of formula IV ($X_2=S$) are prepared as described in U.S. Pat. No. 3,560,550. The formhydroxamates of formula IV ($X_2=O$) are prepared by reacting one mole of a 1-carbamoylformhydroxamyl chloride with two equivalents of an alkoxide of the formula $R_6ONa$ in an inert solvent at a temperature in the range of −70° to −10° C.

Step 2

The reaction of the formimidoyl and thioformimidoyl chlorides of formula V with ammonia or amines can be carried out in water, lower alcohols, benzene, $CH_2Cl_2$ or other solvents, which do not react with ammonia or amines under the reaction conditions employed. Water is preferred since the reaction products often crystallize out and can be isolated by filtration, or can be extracted with a water immiscible solvent. Reaction temperatures of from 0° C to 40° C can be employed. However, higher temperatures should be avoided since mercaptan can be split off from the starting material; thus preferred temperatures are in the range of 15°–30° C.

Process 2

The compounds of formula II wherein
$X_1$ is oxygen,
$X_2$ is sulfur,
$R_1$ and $R_2$ are both other than hydrogen, and
$R_6$ is $R_7$, where
$R_7$ is methyl, ethyl, propyl, isopropyl, n-butyl, allyl, or benzyl,
can also be made by the following two-step process:

Step 1

$$\begin{array}{c}R_1\\ \diagdown\\ N-C-N=C=S + NH_2R_3 \longrightarrow\\ \diagup\\ R_2\\ \text{VI}\end{array} \begin{array}{c}R_1\\ \diagdown\\ N-C-NH-C-NHR_3\\ \diagup\\ R_2\\ \text{VII}\end{array}$$

Step 2

$$\text{VII} + R_7I \longrightarrow \text{II } (X_1=O, X_2=S, R_6=R_7, R_1\neq H, R_2\neq H)$$

Step 1

The synthesis of carbamoylisothiocyanates of formula VI and their conversion to the corresponding 4-thiobiurets of formula VII can be carried out as described by L. A. Spurlock and P. E. Newallis in J. Org. Chem. 33, 2073 (1968).

Step 2

The alkylation of thiobiurets of formula VII can be performed analogous to a method given by M. R. Chaurasis in Agr. Biol. Chem. 32, No. 6, 711 (1968) for alkylation of 6-iodo-2-thio-3-benzylquinazolin-3,4-(1H,3H)-dione to 6-iodo-2-isopropylthio-3-benzyl-4-(3H)-quinazolone.

Process 3

Compounds of formula II wherein $X_1$ is oxygen, and $R_1$ and $R_2$ are both other than hydrogen, can also be made by the following two-step process:

Step 1

$$\text{VI} + 2Cl_2 \longrightarrow \begin{array}{c}R_1\quad O\quad Cl\\ \diagdown\quad \|\quad \diagup\\ N-C-N=C\\ \diagup\quad\quad\diagdown\\ R_2\quad\quad\quad Cl\\ \text{VIII}\end{array}$$

Step 2

$$\text{VIII} \xrightarrow{R_6X_2Na} V \xrightarrow{NH_2R_3} \text{II } (X_1=O)$$

Step 1

The chlorination of isothiocyanates to imidoyldichlorides of formula VIII is known in the art and can be performed analogous to a method given by E. Kuehle et al., Angew. Chem. 79, 663 (1967), who teaches converting dichloroacetylisothiocyanate with chlorine to dichloroacetylcarbonimidoyl dichloride.

Step 2

The stepwise replacement of the two chlorine atoms is best accomplished in alcohols as solvents, in which all reactants are soluble. The reaction temperature must be low in the first step, since imidoyldichlorides react above room temperature with alcohols to carbamates. Preferred temperatures in the first step are −20° to +10° C. Since the second Cl-atom is less reactive than the first, slightly higher reaction temperatures are possible with a preferred range of −10° to 30° C.

Process 4

All compounds of formula II wherein $R_2$ is H, except those wherein $R_1$ is methoxy, can be made as follows:

$$R_1NCX_1 + HN=\overset{\overset{X_2R_6}{|}}{C}-NHR_3 \longrightarrow \text{II } (R_2=H, R_1\neq OCH_3)$$
$$\text{IX}$$

This reaction can be conducted as described in German Patent No. 1,962,797.

Process 5

The compounds of formula II wherein $R_1$ and $R_2$ are H, $X_1$ is oxygen, $X_2$ is sulfur, $R_3$ is hydrogen, and $R_6$ is $R_7$, where $R_7$ is as defined above, can be made as follows:

$$H_2N-\overset{\overset{O}{\|}}{C}-NH-\overset{\overset{S}{\|}}{C}-NH_2 + R_7I \longrightarrow \text{II } (R_1 \text{ and } R_2=H, X_1=O, X_2=S, R_3=H, R_6=R_7)$$
$$X$$

This reaction is performed analogous to step 2 of Process 2. The starting material (X) can be prepared according to U.S. Pat. No. 2,371,113

Process 6

All compounds of formula II can be made as follows:

Step 1

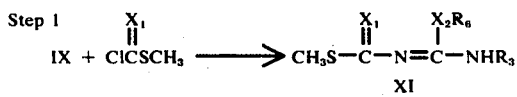

Step 2

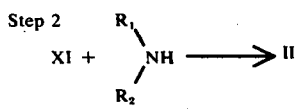

Step 1 is carried out in water or an inert organic solvent in presence of a base such as sodium hydroxide or triethylamine. Temperatures in the range of 0°–50° C and atmospheric pressure are satisfactory.

Step 2 is carried out in an inert organic solvent such as methanol, DMF, DMSO, or acetone at a temperature in the range of about −10° to 100° C; ambient temperature is preferred.

Intermediates of formula III can be prepared by the following processes:

Process 7

All compounds of formula III wherein $R_2$ and $R_3$ are H and Y is $SCH_3$ or Cl can be prepared as follows:

Step 1 is the same as step 1 of Process 6 and is carried out under the same conditions.

Step 2 is carried out in an inert non-polar solvent such as acetonitrile or methylene chloride. A reaction temperature in the range of about 0°–100° C and atmospheric pressure are satisfactory. If desired a catalyst such as triethylamine or dibutyltin dilaurate can be used. When $R_1$ is H, the reactant ($HNCX_1$) is conveniently generated in situ by reaction of an alkali metal isocyanate or thiocyanate and an acid.

Process 8

All compounds of formula III can be prepared as follows:

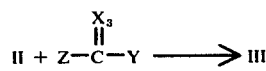

where Z is imidazolyl when Y is imidazolyl and Z is Cl when Y is $SCH_3$ or Cl.

When Y is $SCH_3$ or Cl this reaction is carried out under the conditions given for Process 6, step 1. Example 7 below gives the conditions when Z and Y are both imidazolyl.

Nomenclature of the final products

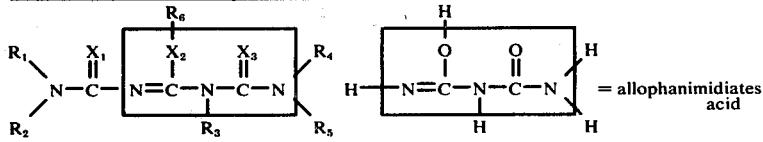

Position: N 1 2 3 4    N 1 2 3 4 for example:

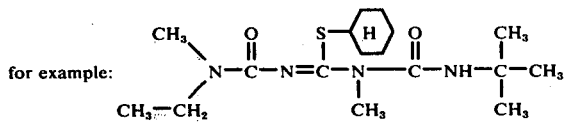

Name: cyclohexyl N-methyl-N-ethylcarbamoyl-2-methyl-4-tertbutylthioallophanimidate It should be kept in mind that, where $R_3$ = H, tautomeric forms of the molecule are possible and do exist:

Step 1

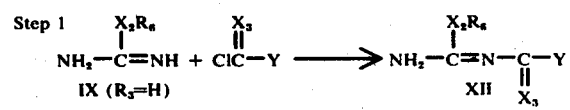

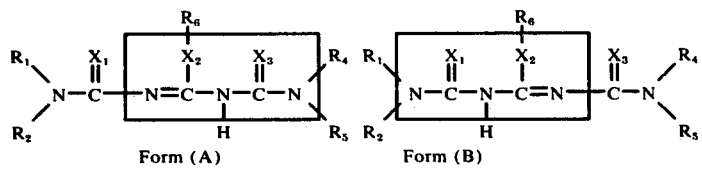

Form (A)     Form (B)

Step 2

XII + $R_1NCX_1$ ⟶ III ($R_2$ and $R_3$=H, Y = $SCH_3$ or Cl)

Both are allophanimidates

If $R_3$ = H, all compounds of this class will still be named as outlined above.

Nomenclature of the intermediates

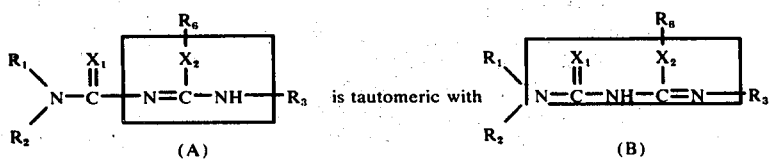

(A) is tautomeric with (B)

Positions: 4 3 2 1 N

Compound (A) is a pseudourea derivative; Compound (B) is an allophanimidate. Since the name of Compound (B) covers a longer chain, all intermediates existing in either form (A) or (B) are hereafter called allophanimidates. for example:

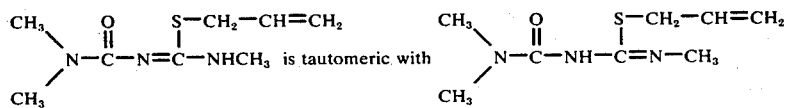

Name: allyl N-methyl-4,4-dimethylthioallophanimidate

The compounds of this invention can also exist in geometrically isomeric forms (cis and trans or syn and anti) as shown in structures C and D.

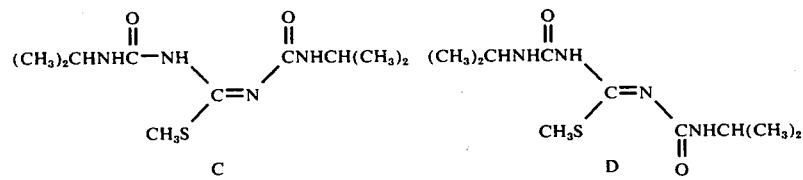

Compound C and D have different physical properties such as infrared spectra.

Formulation and Use of the Compounds

The compounds of formula I are useful as herbicides. They may be used at rates of 2.5 to 40 kilogram/hectare to control all vegetation in industrial sites, along rights-of-way, pipelines, tank farms, and the like. At rates of 0.125 to 8 kilogram/hectare certain of these compounds can be used for selective weed control in many crops including asparagus, soybeans, stone fruits, pineapple, sugarcane, sisal, alfalfa, and corn. The precise rate of material to use in any situation will depend upon the weeds to be controlled, climatic and edaphic conditions and whether selective weed control is desired.

The compounds of this invention may be combined with all other herbicides and are particularly useful in combination with bromacil (3-sec-butyl-5-bromo-6-methyluracil), diuron (3-/3,4-dichlorophenyl/-1,1-dimethylurea), paraquat (1,1'-dimethyl-4,4'-bipyridinium ion), 1,1-dimethyl-3,3-(N-tert-butylcarbamoyloxyphenyl)urea, 4-amino-6-tert-butyl-3-methyl-thio-as-triazin-5(4H)-one, and the S-triazines such as 2-chloro-4-ethylamino-6-iospropylamino-S-triazine, for controlling a broad spectrum of weeds.

The compounds of formula I can be formulated for herbicidal use in the various ways which are conventional for herbicides of similar physical properties. Useful formulations include wettable powders, oil suspensions and solutions, aqueous dispersions, dusts, granules, pellets, and high strength compositions. Broadly speaking, these formulations consist essentially of about 1 to 99% by weight of herbicidally active material (including at least one compound of formula I in a herbicidally effective amount) and at least one of (a) about 0.1 to 20% by weight of surface active agent and (b) about 5 to 99% by weight of essentially biologically inert solid or liquid diluent. More specifically, the various types of formulations will generally contain these ingredients in the following approximate proportions.

|  | Percent By Weight | | |
|---|---|---|---|
|  | Herbicide | Diluent | Surfactant |
| Wettable Powders | 25 – 90 | 0 – 74 | 1 – 10 |
| Oil Suspensions or Solutions | 5 – 35 | 55 – 94 | 1 – 10 |
| Aqueous Dispersions | 10 – 50 | 40 – 89 | 1 – 10 |
| Dusts | 1 – 25 | 70 – 99 | 0 – 5 |
| Granules and Pellets | 1 – 35 | 65 – 99 | 0 – 15 |
| High Strength Compositions | 90 – 99 | 0 – 10 | 0 – 2 |

The actual percentages that can be realized with a particular compound of formula I will depend upon its physical properties.

The manner of making and using such herbicidal formulations is described in numerous patents. See, for example, Luckenbaugh U.S. Pat. No. 3,309,192, Loux U.S. Pat. No. 3,235,357, Todd U.S. Pat. No. 2,655,445, Hamm et al. U.S. Pat. No. 2,863,752, Scherer et al. U.S. Pat. No. 3,079,244, Gysin et al. U.S. Pat. No. 2,891,855, and Barrous U.S. Pat. No. 2,642,354.

While conventional application of sprayable formulations have usually been made in a dilute form (for example at a rate of about 200 liters pe hectare or more), the compounds of formula I can also be applied at higher concentrations in the typical "ultra-low-volume" (ULV) or "low volume" applications from aircraft or ground sprayers. For this purpose wettable powders can be dispersed in small amounts of aqueous or nonaqueous carrier. The emulsifiable concentrate suspensions can be used directly or with minor dilution. Special compositions, particularly suitable for ULV applications are solutions or finely divided suspensions in one or more carrier such as petroleum oils, dialkylformamides, N-alkylpyrrolidones, and dimethylsulfoxide.

Herbicidal activity of the compounds of this invention was discovered in a greenhouse test. Seeds of crabgrass (*Digitaria spp.*), barnyardgrass (*Echinochloa crusgalli*), wild oats (*Avena fatua*), *Cassia tora*, morningglory (*Ipomoea spp.*), mustard (*Brassiea spp.*), marigold (*Tagetes spp.*), dock (*Rumex crispus*), and nutsedge (*Cyperus rotundus*) tubers were planted in sand or soil and treated preemergence with the chemicals dissolved in a solvent. At the same time johnsongrass (*Sorghum halepense*) having four leaves, crabgrass and barnyardgrass with three leaves and nutsedge from tubers with two leaves were treated postemergence. Treatment rates are indicated in the following Table. Treated plants and controls were maintained in a greenhouse for sixteen days, then all species were compared to controls and visually rated for responses to treatment. A qualitative rating (type of injury) was made; the letter C was used to indicate chlorosis, and the letter G to indicate growth retardation. A quantitative rating was also made on a scale of 0 to 10; a rating of 0 means no effect and a rating of 10 means maximum effect, e.g. complete kill. Ratings, in this test for some highly active compounds of this invention follow:

tation. When all has been added, the suspension of crystals which forms is stirred for 10 minutes to assure completion of the reaction. The reaction mass is then cooled to 0° C., the solids filtered and recrystallized from acetone to give 10.6 parts of methyl 4,4-dimethylthioallophanimidate (a compound of formula II), m.p. 136°–138° C.

A mixture of 7 parts methyl 4,4-dimethylthioallophanimidate, 8 parts of t-butylisocyanate and 50 ml methylene chloride is refluxed for 2 hours. After standing overnight at room temperature, the solution is evaporated under vacuum to give a viscous oil, which solidified after trituration with petroleum-ether. Recrystallization from petroleum-ether gives methyl N-dimethylcarbamoyl-4-tert-butylthioallophanimidate, (a Table

| Compound | Lb. Per Acre | Postemergence | | | | Preemergence | | | | | | | | |
|---|---|---|---|---|---|---|---|---|---|---|---|---|---|---|
| | | Nuts-edge | John-son-grass | Crab-grass | Barn-yard grass | Crab-grass | Barn-yard grass | Wild Oats | Nuts-edge | Cas-sie | Morn-ing glory | Mus-tard | Mari-gold | Dock |
| methyl N-isopropyl carbamoyl-4-isopropyl- thioallophanimidate | 10 | 10C | 10C | 10C | 10C | 10C | 9C | 10C | 5C | 10C | 10C | 10C | 10C | 10C |
| | 2 | | | | | 9C | 9C | 10C | 5C | 10C | 10C | 10C | 10C | 10C |
| | 2 | 8C | 10C | 10C | 10C | 10C | 10C | 10C | 4C | 10C | 10C | 10C | 10C | 10C |
| | 1 | 7C | 10C | 10C | 10C | | | | | | | | | |
| | 0.4 | | | | | 10C | 10C | 10C | 1C | 10C | 10C | 10C | 10C | 10C |
| methyl N-tert-butyl- carbamoyl-4-tert-butyl- thioallophanimidate | 10 | 10C | 10C | 10C | 10C | 10C | 10C | 10C | 5C | 10C | 10C | 10C | 10C | 10C |
| | 2 | | | | | 10C | 10C | 10C | 5C | 10C | 10C | 10C | 10C | 10C |
| | 2 | 10C | 10C | 9C | 10C | | | | | | | | | |
| | 0.4 | 6C | 5C | 7C | 4C | | | | | | | | | |
| methyl N-sec-butyl- carbamoyl-4-sec-butyl- thioallophanimidate | 10 | 9C | 10C | 10C | 10C | 10C | 10C | 10C | 6C | 10C | 10C | 10C | 10C | 10C |
| | 2 | | | | | 10C | 10C | 10C | 5C | 10C | 10C | 10C | 10C | 10C |
| | 1 | 10C | 10C | 10C | 10C | | | | | | | | | |
| methyl N-methyl- carbamoyl-4-isopropyl- thioallophanimidate | 10 | 9C | 10C | 10C | 10C | 10C | 9C | 10C | 6C | 10C | 10C | 10C | 10C | 10C |
| | 2 | | | | | 10C | 10C | 10C | 9C | 10C | 10C | 10C | 10C | 10C |
| | 1 | 8C | 10C | 10C | 10C | | | | | | | | | |
| | 0.2 | 0 | 10C | 10C | 7C | | | | | | | | | |
| methyl N-methyl- carbamoyl-4-cyclohexyl- thioallophanimidate | 10 | 9C | 10C | 10C | 10C | 10C | 10C | 10C | 9C | 10C | 10C | 10C | 10C | 10C |
| | 2 | | | | | 10C | 10C | 10C | 5C | 10C | 10C | 10C | 10C | 10C |
| | 1 | 0 | 10C | 10C | 7C | | | | | | | | | |
| methyl N-diethyl- carbamoyl-4-allylthio- allophanimidate | 10 | 10C | 10C | 10C | 10C | 9C | 10C | 10C | 5C | 10C | 10C | 10C | 10C | 9C |
| | 2 | | | | | 9C | 9C | 10C | 2C | 10C | 10C | 10C | 10C | 9C |
| methyl N-dimethyl- carbamoyl-4-tert-butyl- thioallophanimidate | 10 | 9C | 10C | 10C | 10C | 9C | 9C | 10C | 4C | 10C | 10C | 10C | 10C | 10C |
| | 2 | | 10C | 10C | 9C | 9C | 9C | 10C | 2C | 10C | 10C | 10C | 10C | 10C |
| | 2 | 2G | 10C | 9C | 10C | 10C | 10C | 10C | 3C | 10C | 10C | 10C | 10C | 10C |
| | 0.4 | | | | | 10C | 10C | 10C | 0 | 10C | 10C | 10C | 10C | 10C |
| methyl N-butyl- carbamoyl-4-butylthio- allophanimidate | 10 | 9C | 10C | 10C | 10C | 10C | 9C | 10C | 7C | 10C | 10C | 10C | 10C | 10C |
| | 2 | | | | | 10C | 9C | 10C | 5C | 10C | 10C | 10C | 10C | 10C |
| | 1 | 10C | 5C | 7C | 3C | | | | | | | | | |
| methyl N-dimethyl- carbamoyl-4,4-dimethyl- thioallophanimidate | 2 | 0 | 4C | 1C | 2C | 9C | 9C | 7C | 0 | 10C | 10C | 10C | 10C | 9C |
| | 0.4 | | | | | 7C | 5C | 3C | — | 3C | 5C | 10C | 3C | 8C |
| methyl N-(1-pyrrolidonyl)- carbonyl-4-isopropyl- thioallophanimidate | 2 | 0 | 0C | 10C | 10C | 9C | 10C | 10C | 4C | 10C | 10C | 10C | 10C | 10C |
| | 0.4 | | | | | 9C | 10C | 10C | 0 | 10C | 10C | 10C | 10C | 9C |
| methyl N-ethylcarbamoyl- 4-(1-phenylethyl)thio- allophanimidate | 2 | 0 | 5C | 7C | 9C | 10C | 10C | 10C | 5C | 10C | 10C | 10C | 10C | 10C |
| | 0.4 | | | | | 10C | 10C | 10C | 2C | 10C | 10C | 10C | 10C | 10C |
| methyl N-methyl- carbamoyl-4-tert-butyl- allophanimidate | 2 | 2G | 9C | 9C | 10C | 10C | 10C | 10C | 2C | 10C | 10C | 10C | 10C | 10C |
| | 0.4 | | | | | 10C | 10C | 10C | 0 | 10C | 10C | 10C | 10C | 10C |

EXAMPLE 1

To a suspension of 162.2 parts of methyl dimethylcarbamoylthioformhydroxamate (a compound of formula IV) in 570 parts of methylene chloride are gradually added within 20 min. at 10° C, 119 parts of thionyl chloride. HCl-gas is evolved and a solution is formed at the end of the SOCl₂ addition. After evaporation of the solvent and removal of lower boiling methylthiocyanate and dimethylcarbamoyl chloride by distillation at reduced pressure, the N-dimethylcarbamoyl-1-methylthioformimidoyl chloride (a compound of formula V) is distilled at 85° C/0.4 mm.

To 50 parts of conc. aqueous ammonia are added within 10 min. at 20°–25° C., 18.1 parts of N-dimethylcarbamoyl-1-methylthioformimidoyl chloride with agicompound of formula I), m.p. 74°–78° C.

By using the appropriate reactants, the following illustrative compounds of formulae I, II and V can be prepared similarly:

Compounds of Formula V

N-methylethylcarbamoyl-1-methylthioformimidoyl chloride

N-methylbutylcarbamoyl-1-methylthioformimidoyl chloride

N-diethylcarbamoyl-1-methylthioformimidoyl chloride

N-dibutylcarbamoyl-1-methylthioformimidoyl chloride

N-diallylcarbamoyl-1-methylthioformimidoyl chloride

N-pentamethylenecarbamoyl-1-methylthioformimidoyl chloride
N-diethyleneoxycarbamoyl-1-methylthioformimidoyl chloride
N-methylethylcarbamoyl-1-ethylthioformimidoyl chloride
N-methylbutylcarbamoyl-1-isopropylthioformimidoyl chloride
N-diethylcarbamoyl-1-butylthioformimidoyl chloride
N-dibutylcarbamoyl-1-cyclohexylthioformimidoyl chloride
N-diallylcarbamoyl-1-ethylthioformimidoyl chloride
N-pentamethylenecarbamoyl-1-ethylthioformimidoyl chloride
N-diethyleneoxycarbamoyl-1-propylthioformimidoyl chloride Compounds of Formula II methyl 4-methyl-4-ethylthioallophanimidate
methyl 4-methyl-4-butylthioallophanimidate, m.p. 74°–76° C.
methyl 4,4-diethylthioallophanimidate
methyl 4,4-dibutylthioallophanimidate
methyl 4,4-diallylthioallophanimidate
methyl 4,4-tetramethylenethioallophanimidate, m.p. 179°–181° C
methyl N-octyl-4,4-dimethylthioallophanimidate
methyl N-sec-butyl-4-methyl-4-ethylthioallophanimidate
methyl N,4-dibutyl-4-methylthioallophanimidate
methyl N-isopropyl-4,4-diethylthioallophanimidate
methyl N-propyl-4,4-dibutylthioallophanimidate
methyl N-ethyl-4,4-dibutylthioallophanimidate
methyl N,4,4-trimethylthioallophanimidate
methyl N-methyl-4,4-hexamethylenethioallophanimidate
methyl N-methyl-4,4-diethylenoxythioallophanimidate
ethyl 4-methyl-4-ethylthioallophanimidate
isopropyl 4-methyl-4-butylthioallophanimidate
butyl 4,4-diethylthioallophanimidate
benzyl 4,4-dibutylthioallophanimidate
sec-butyl 4,4-diallylthioallophanimidate
ethyl 4,4-tetramethylenethioallophanimidate
ethyl N-octyl-4,4-dimethylthioallophanimidate
butyl N-sec-butyl-4-methyl-4-ethylthioallophanimidate
ethyl N,4-dibutyl-4-methylthioallophanimidate
cyclohexyl N-isopropyl-4,4-diethylthioallophanimidate
isopropyl N-propyl-4,4-dibutylthioallophanimidate Compounds of Formula I methyl N-dimethylcarbamoyl-4-methylthioallophanimidate, m.p. 112°–113° C
methyl N-dimethylcarbamoyl-4-ethylthioallophamimidate, m.p. 95°–97° C
methyl N-dimethylcarbamoyl-4-propylthioallophanimidate, m.p. 66°–74° C
methyl N-dimethylcarbamoyl-4-isopropylthioallophanimidate, m.p. 86°–89° C
methyl N-dimethylcarbamoyl-4-butylthioallophanimidate, $n_D^{20}$ 1.5530
methyl N-dimethylcarbamoyl-4-octylthioallophanimidate, $n_D^{20}$ 1.5322
methyl N-dimethylcarbamoyl-4-allylthioallophanimidate, m.p 55°–58° C
methyl N-dimethylcarbamoyl-4-propynylthioallophanimidate
methyl N-dimethylcarbamoyl-4-cyclohexylthioallophanimidate, m.p. 88°–91° C
methyl N-dimethylcarbamoyl-4-cyclohexylmethylthioallophanimidate
methyl N-dimethylcarbamoyl-4-norbornylthioallophanimidate
methyl N-dimethylcarbamoyl-4-phenylthioallophanimidate, m.p. 122°–123° C
methyl N-dimethylcarbamoyl-4-(o-fluorophenyl)thioallophanimidate, m.p. 125°–127° C
methyl N-dimethylcarbamoyl-4-(3,4-dichlorophenyl)thioallopahimidate, m.p. 154°–155° C
methyl N-dimethylcarbamoyl-4-(p-methoxyphenyl)-thioallophanimidate, m.p. 126°–127° C
methyl N-methylethylcarbamoyl-4-tert-butylthioallophanimidate
methyl N-methylbutylcarbamoyl-4-allylthioallophanimidate
methyl N-diallylcarbamoyl-4-methylthioallophanimidate
methyl N-dibutylcarbamoyl-4-methylthioallophanimidate
methyl N-dibutylcarbamoyl-4-phenylthioallophanimidate
methyl N-dibutylcarbamoyl-4-(3,4-dichlorophenyl)-thioallophanimidate
methyl N-pentamethylenecarbamoyl-4-tert-butylthioallophanimidate
ethyl N-dimethylcarbamoyl-4-methylthioallophanimidate, m.p. 109°–111° C
ethyl N-dimethylcarbamoyl-4-ethylthioallophanimidate
isopropyl N-dimethylcarbamoyl-4-propylthioallophanimidate
cyclohexyl N-dimethylcarbamoyl-4-isopropylthioallophanimidate
isopropyl N-dimethylcarbamoyl-4-butylthioallophanimidate
ethyl N-dimethylcarbamoyl-4-octylthioallophanimidate
allyl N-dimethylcarbamoyl-4-allylthioallophanimidate
cyclopentyl N-dimethylcarbamoyl-4-propynylthioallophanimidate
isopropyl N-dimethylcarbamoyl-4-cyclohexylthioallophanimidate
hexyl N-dimethylcarbamoyl-4-cyclohexylmethylthioallophanimidate
ethyl N-dimethylcarbamoyl-4-phenylthioallophanimidate
methyl N-dimethylcarbamoyl-4-tert-butyl-1,3-dithioallophanimidate
methyl N-dibutylcarbamoyl-4-methyl-1,3-dithioallophanimidate
methyl N-dimethylcarbamoyl-4-cyclohexyl-1,3-dithioallophanimidate
methyl N-diallylcarbamoyl-4-phenyl-1,3-dithioallophanimidate
methyl N-dimethylcarbamoyl-4-(3,4-dichlorophenyl)-1,3-dithioallophanimidate
methyl N-dimethylcarbamoyl-2-methyl-4-(3,4-dichlorophenyl)-thioallophanimidate, m.p. 87°–89° C.
methyl N-dimethylcarbamoyl-2-methyl-4-phenylthioallophanimidate methyl N-dimethylcarbamoyl-2-methyl-4-(o-fluorophenyl)thioallophanimidate, m.p. 74°–77° C.
methyl N-dimethylcarbamoyl-2-methyl-4-(p-methoxyphenyl)thioallophanimidate
methyl N-dimethylcarbamoyl-2-methyl-4-(p-bromophenyl)thioallophanimidate, m.p. 98°–99° C.
methyl N-dimethylcarbamoyl-2-ethyl-4-(p-cyanophenyl)thioallophanimidate
methyl N-dimethylcarbamoyl-2-ethyl-4-(p-cumenyl)thioallophanimidate
methyl N-dimethylcarbamoyl-2-propyl-4-(p-nitrophenyl)thioallophanimidate
methyl N-dimethylcarbamoyl-2-isopropyl-4-(m-chlorophenyl)thioallophanimidate
methyl N-dimethylcarbamoyl-2-sec-butyl-4-(3,5-dichlorophenyl)thioallophanimidate
methyl N-dimethylcarbamoyl-2-butyl-4-(p-trifluoromethylphenyl)thioallophanimidate
methyl N-methylethylcarbamoyl-2-methyl-4-phenylthioallophanimidate
methyl N-methylbutylcarbamoyl-2-butyl-4-(o-fluorophenyl)thioallophanimidate
methyl N-diethylcarbamoyl-2-isopropyl-4-(p-cyanophenyl)thioallophanimidate
methyl N-dibutylcarbamoyl-2-propyl-4-(p-bromophenyl)thioallophanimidate
methyl N-dibutylcarbamoyl-2-ethyl-4-(m-chlorophenyl)thioallophanimidate
methyl N,N-pentamethylenecarbamoyl-2-methyl-4-phenylthioallophanimidate
methyl N,N-diethylenoxycarbamoyl-2-methyl-4-phenylthioallophanimidate
ethyl N-dimethylcarbamoyl-2-methyl-4-phenylthioallophanimidate
isopropyl N-dimethylcarbamoyl-2-methyl-4-(o-fluorophenyl)thioallophanimidate
cyclohexyl N-dimethylcarbamoyl-2-methyl-4-(p-methoxyphenyl)thioallophanimidate
ethyl N-dimethylcarbamoyl-2-methyl-4-(p-bromophenyl)thioallophanimidate
propyl N-dimethylcarbamoyl-2-ethyl-4-(p-cyanophenyl)thioallophanimidate
ethyl N-dimethylcarbamoyl-2-ethyl-4-(p-cumenyl)thioallophanimidate
hexyl N-dimethylcarbamoyl-2-propyl-4-(p-nitrophenyl)thioallophanimidate
propyl N-dimethylcarbamoyl-2-isopropyl-4-(m-chlorophenyl)thioallophanimidate
ethyl N-dimethylcarbamoyl-2-sec-butyl-4-(3,5-dichlorophenyl)thioallophanimidate

EXAMPLE 2

To a solution of 65 parts of dimethylcarbamoylisothiocyanate (a compound of formula VI) in 350 parts methylene chloride are added within 10 minutes at 0° C, 50 parts of conc. aqueous ammonia with good agitation. The resulting slurry of crystals is stirred for an additional 15 minutes at 0° C and then filtered to give 70 parts of 1,1-dimethyl-4-thiobiuret (a compound of formula VII), m.p. 184°–185° C.

To a solution of 58.5 parts of 1,1-dimethyl-4-thiobiuret in 200 parts of water, 200 parts of methanol and 32 parts of 50% aqueous sodium hydroxide are added at 25° C. within 10 minutes 62.5 parts of iodoethane. The reaction mass is then stirred at 25° C. for 2 hours. Evaporation of the methanol and part of the water under vacuum gives 64 parts of crude ethyl 4,4-dimethylthioallophanimidate (a compound of formula II), which is recrystallized from water-methanol (50:50) and shows a melting point of 90°–93° C.

A solution of 5 parts of ethyl 4,4-dimethylthioallophanimidate and 1.8 parts of methylisocyanate in 70 parts of methylene chloride was refluxed for 2 hours. After evaporation of the solvent, the residue was recrystallized from ethylacetate to give ethyl N-dimethylcarbamoyl-4-methylthioallophanimidate (a compound of formula I), m.p. 109°–111.5° C.

By using the appropriate reactants, the following illustrative compounds of formulae I and II can be prepared similarly:

Compounds of Formula II propyl 4,4-dimethylthioallophanimidate
benzyl 4,4-dimethylthioallophanimidate
ethyl N,4,4-trimethylthioallophanimidate
butyl N-ethyl-4,4-dimethylthioallophanimidate
propyl N-propyl-4,4-dimethylthioallophanimidate
ethyl N-isopropyl-4,4-dimethylthiocallophanimidate
isopropyl N-butyl-4,4-dimethylthioallophanimidate
propyl 4,4-diethylthioallophanimidate
isopropyl 4,4-dipropylthioallophanimidate
butyl 4,4-dibutylthioallophanimidate
benzyl 4-ethyl-4-methylthioallophanimidate
butyl N-ethyl-4-isopropyl-4-methylthioallophanimidate
propyl N-propyl-4,4-diisopropylthioallophanimidate
ethyl N-isopropyl-4,4-diethylthioallophanimidate
isopropyl N-butyl-4,4-dibutylthioallophanimidate
ethyl 4,4-dimethylthioallophanimidate
isopropyl 4,4-dimethylthioallophanimidate
allyl 4,4-dimethylthioallophanimidate
butyl 4,4-dimethylthioallophanimidate
benzyl 4,4-dimethylthioallophanimidate
methyl N-allyl-4,4-dimethylthioallophanimidate
methyl N-propargyl-4,4-dimethylthioallophanimidate

COMPOUNDS OF FORMULA I propyl N-dimethylcarbamoyl-4-methylthioallophanimidate, m.p. 82°–84° C
isopropyl N-dimethylcarbamoyl-4-allylthioallophanimidate
ethyl N-dimethylcarbamoyl-2-phenylthioallophanimidate
butyl N-dimethylcarbamoyl-2-ethyl-4-(3,4-dichlorophenyl)thioallophanimidate
propyl N-dimethylcarbamoyl-2-propyl-4-(p-butylphenyl)thioallophanimidate
ethyl N-dimethylcarbamoyl-2-isopropyl-4-(m-chlorophenyl)thioallophanimidate
isopropyl N-dimethylcarbamoyl-2-butyl-4-(3,5-dichlorophenyl)thioallophanimidate
propyl N-diethylcarbamoyl-4-methylthioallophanimidate
isopropyl N-dipropylcarbamoyl-4-allylthioallophanimidate
benzyl N-diethylcarbamoyl-4-tert-butylthioallophanimidate
butyl N-dipropylcarbamoyl-4-tert-butylthioallophanimidate
ethyl N-dimethylcarbamoyl-4-tert-butylthioallophanimidate, m.p. 92°–94° C
propyl N-dimethylcarbamoyl-4-tert-butylthioallophanimidate, m.p. 102°–104° C
isopropyl N-dimethylcarbamoyl-4-tert-butylthioallophanimidate, wax methyl N-dimethylcarbamoyl-2-allyl-4-(phenyl)thioallophanimidate,
methyl N-dimethylcarbamoyl-2-propynyl-4-(phenyl)thioallophanimidate
allyl N-dimethylcarbamoyl-4-tert-butylthioallophanimidate, m.p. 96°–98° C
butyl N-bimethylcarbamoyl-4-tert-butylthioallophanimidate, m.p. 124°–126° C

EXAMPLE 3

To a solution of 130 parts of dimethylcarbamoylisothiocyanate (a compound of formula VI), in 700 parts of methylene chloride at 0° C are added within 1 hour 142 parts of chlorine gas. The resulting red solution is then evaporated under vacuum to give crude dimethylcarbamoylformimidoyl dichloride (a compound of formula VIII) as residue, which is then purified by distillation, b.p. 52° C/0.4 mm.

A sodium cyclohexylmercaptide solution, prepared from 5.4 parts of sodium methylate and 11.6 parts of cyclohexylmercaptan in 100 ml. methanol by refluxing for 10 minutes, is added at −10° C. to a solution of 16.9 parts of dimethylcarbamoylformimidoyl dichloride in 50 ml methanol, prepared at −10° C. After stirring the reaction mixture for 10 minutes at −10° C. (NaCl present), 5 parts of gaseous ammonia are sparged into the mixture at −10° C. and then the temperature allowed to rise to 30° C. When the temperature has fallen back to 25° C., the NaCl is filtered and the filtrate evaporated. For purification, the product is then dissolved in methylene chloride and repeatedly extracted with dilute aqueous hydrochloric acid. The HCL-extracts are combined, and after filtration through Celite, the pH is adjusted to 7 by the addition of sodium hydroxide. After cooling to 0° C., the precipitated solids are isolated by filtration and are purified by recrystallization from petroleum-ether to give pure cyclohexyl 4,4-dimethylthioallophanimidate (a compound of formula II), m.p. 84.5°–86° C.

A mixture of 5 parts of cyclohexyl 4,4-dimethylthioallophanimidate and 4 parts t-butylisocyanate in 70 parts of methylene chloride is refluxed for 2 hours. After evaporation of the solvent, the oily residue is triturated with petroleum-ether to give solids, which are recrystallized from cyclohexane to give pure cyclohexyl N-dimethylcarbamoyl-4-t-butylthioallophanimidate (a compound of formula I).

By using the appropriate reactants, the following illustrative compounds of formulae I and II can be prepared similarly:

Compounds of Formula II allyl 4,4-dimethylthioallophanimidate
sec-butyl 4,4-dimethylthioallophanimidate
phenyl 4,4-dimethylthioallophanimidate
cyclohexyl N,4,4-trimethylthioallophanimidate
allyl N-butyl-4,4-dimethylthioallophanimidate
sec-butyl N-isopropyl-4,4-dimethylthioallophanimidate
sec-butyl 4,4-diethylthioallophanimidate
phenyl 4,4-diethylthioallophanimidate
cyclohexyl N-methyl-4,4-dipropylthioallophanimidate
allyl N-butyl-4,4-dibutylthioallophanimidate
sec-butyl N-isopropyl-4,4-diisopropylthioallophanimidate
allyl N-(2-butynyl)-4,4-dimethylthioallophanimidate
cyclooctyl-4,4-dimethylthioallophanimidate
2-octenyl-4,4-dimethylthioallophanimidate

COMPOUNDS OF FORMULA I allyl N-dimethylcarbamoyl-4-tert-butylthioallophanimidate
allyl N-dimethylcarbamoyl-4-methylthioallophanimidate
sec-butyl N-dimethylcarbamoyl-4-tert-butylthioallophanimidate
cyclohexyl N-dimethylcarbamoyl-4-tert-butylthioallophanimidate
phenyl N-dimethylcarbamoyl-4-tert-butylthioallophanimidate
cyclohexyl N-dimethylcarbamoyl-4-allylthioallophanimidate
allyl N-dimethylcarbamoyl-4-allylthioallophanimidate
sec-butyl N-dimethylcarbamoyl-4-allylthioallophanimidate
allyl N-dimethylcarbamoyl-4-cyclohexylthioallophanimidate
sec-butyl N-dimethylcarbamoyl-4-cyclohexylthioallophanimidate
cyclohexyl N-dimethylcarbamoyl-4-cyclohexylthioallophanimidate
allyl N-dimethylcarbamoyl-2-(2-butynyl)-4-phenylthioallophanimidate
sec-butyl N-dimethylcarbamoyl-2-isopropyl-4-(3,4-dichlorophenyl)thioallophanimidate
cyclohexyl N-dimethylcarbamoyl-2-methyl-4-(m-chlorophenyl)thioallophanimidate
cyclohexyl N-diethylcarbamoyl-4-tert-butylthioallophanimidate
phenyl N-diethylcarbamoyl-4-tert-butylthioallophanimidate
cyclohexyl N-dipropylcarbamoyl-4-allylthioallophanimidate
allyl N-isopropyl-N-methylcarbamoyl-4-allylthioallophanimidate
sec-butyl N-diethylcarbamoyl-4-allylthioallophanimidate
allyl N-diethylcarbamoyl-4-cyclohexylthioallophanimidate
allyl N-diethylcarbamoyl-2-butyl-4-phenylthioallophanimidate
sec-butyl N-diethylcarbamoyl-2-isopropyl-4-(3,4-dichlorophenyl)-thioallophanimidate
methyl N-dimethylcarbamoyl-4-benzylthioallophanimidate
cyclooctyl N-dimethylcarbamoyl-4-isopropylthioallophanimidate
2-octenyl N-dimethylcarbamoyl-4-isopropylthioallophanimidate

EXAMPLE 4

To a solution of 16.9 parts of dimethylcarbamoylformimidoyl dichloride (a compound of formula VIII) in 25 ml methanol, prepared at −10° C, is added within 10 minutes at −10° C, a solution of 5.4 parts sodium methylate in 150 ml methanol. Sodium chloride precipitates. The reaction mixture is stirred for 10 minutes at −10° C and then 5 parts of gaseous ammonia are sparged into the mixture at −10° C. The temperature is then allowed to rise to 25° C, the methanol evaporated under vacuum, and the residue triturated with methylene chloride. After filtration of the inorganic salts, the methylene chloride filtrate is evaporated and the residue recrystallized from a little water to give pure methyl 4,4-dimethylallophanimidate (a compound of formula II), m.p. 80°–82.5° C.

5 Parts of methyl 4,4-dimethylallophanimidate and 20 ml of t-butylisocyanate are refluxed overnight. The next day, the solution is evaporated to give an oil, which crystallizes when tirturated with petroleum-ether under cooling. In order to remove some unreacted starting material and byproducts, the solids are first triturated with water and filtered. After drying, the solids are then triturated with carbon tetrachloride and impurities removed by filtration. The carbon tetrachloride filtrate is then evaporated and the residue recrystallized from petroleum-ether to give pure methyl N-dimethylcarbamoyl-4-t-butylallophanimidate (a compound of Formula I), m.p. 96°–98° C.

By using the appropriate reactants, the following illustrative compounds of formula I and II can be prepared similarly:

Compounds of Formula II ethyl 4,4-dimethylallophanimidate
isopropyl 4,4-dimethylallophanimidate
propyl, 4,4-dimethylallophanimidate
allyl 4,4-dimethylallophanimidate
butyl 4,4-dimethylallophanimidate
cyclohexyl 4,4-dimethylallophanimidate
methyl N, 4,4-trimethylallophanimidate
propyl N,4,4-trimethylallophanimidate
methyl N-butyl-4,4-dimethylallophanimidate
ethyl 4,4-diethylallophanimidate
isopropyl 4,4-diethylallophanimidate
propyl 4,4-dibutylallophanimidate
allyl 4,4-diisopropylallophanimidate
butyl 4,4-diethylallophanimidate
cyclohexyl 4,4-dibutylallophanimidate Compounds of Formula I ethyl N-dimethylcarbamoyl-4-tert-butylallophanimidate
isopropyl N-dimethylcarbamoyl-4-allylallophanimidate
propyl N-dimethylcarbamoyl-4-cyclohexylallophanimidate
butyl N-dimethylcarbamoyl-4-isopropylallophanimidate
cyclohexyl N-dimethylcarbamoyl-4-tert-butylallophanimidate
methyl N-dimethylcarbamoyl-2-methyl-4-phenylallophanimidate
propyl N-dimethylcarbamoyl-2-methyl-4-(3,4-dichlorophenyl)-allophanimidate
methyl N-dimethylcarbamoyl-2-butyl-4-(p-methoxyphenyl)allophanimidate

EXAMPLE 5

2 Parts of methyl 4-isopropylallophanimidate (a compound of formula II) and 5 parts of isopropyl isocyanate are stirred overnight at room temperature in 5 parts methylene chloride with a catalytic amount of dibutyltin dilaurate. The solvent is removed under reduced pressure to give a solid residue which is recrystallized from hexane: chlorobutane (1:1). 1.5 Parts of pure methyl N-isopropylcarbamoyl-4-isopropylallophanimidate (a compound of formula I), m.p. 86°–89° C, is collected.

Using an appropriate compound of the formula II from the list below and an appropriate isocyanate, each compound of formula I listed below can be prepared similarly:

Compounds of Formula II methyl 4-tert-butylallophanimidate
methyl 4-cyclohexylallophanimidate
methyl 4-cyclooctylallophanimidate
methyl 4-octyallophanimidate
methyl 4-allylallophanimidate
methyl 4-cyclopentylallophanimidate
methyl 4-cyclopropylallophanimidate
methyl 4-cyclopropylmethylallophanimidate
methyl 4-cyclohexylmethylallophanimidate
methyl 4-(2-cyclooctylethyl)allophanimidate
methyl 4-(norborn-2-yl)allophanimidate
methyl 4-propargylallophanimidate
methyl 4-(but-2-ynyl)allophanimidate
methyl 4-methoxyallophanimidate
methyl 4-(2-chloroethyl)allophanimidate
methyl 4-(1,2,2-trichloroethyl)allophanimidate
methyl 4-(2-bromoethyl)allophanimidate
methyl 4-(2-iodoethyl)allophanimidate
methyl 4-trifluoromethylallophanimidate
methyl 4-fluoromethylallophanimidate
methyl 4-(2-methoxyethyl)allophanimidate
methyl 4-ethoxymethylallophanimidate
methyl 4-methylallophanimidate
methyl 4-ethylallophanimidate
ethyl 4-butylallophanimidate
methyl 4-benzylallophanimidate
methyl 4-(2-ethylthioethyl)allophanimidate
methyl 4-(2-cyanoethyl)allophanimidate
methyl 4-methoxycarbonylmethylallophanimidate
methyl 4-acetonylallophanimidate
methyl 4-(2-chlorocyclohexyl)allophanimidate
methyl 4-(3-bromocyclohexyl)allophanimidate
methyl 4-(2-methylcyclohexyl)allophanimidate
methyl 4-(3,4-dimethylcyclopentyl)allophanimidate
methyl 4-(4-butylcyclohexyl)allophanimidate
methyl 4-(2-ethylcyclopropyl)allophanimidate
methyl 4-sec-butylallophanimidate
methyl 4-phenylallophanimidate Compounds of Formula I methyl N-tert-butylcarbamoyl-4-tert-butylallophanimidate, m.p. 120°–122° C
methyl N-cyclohexylcarbamoyl-4-cyclohexylallophanimidate
methyl N-methylcarbamoyl-4-cyclooctylallophanimidate
methyl N-octylcarbamoyl-4-ethylallophanimidate
methyl N-allylcarbamoyl-4-allylallophanimidate, m.p. 88°–90° C
methyl N-cyclopentylcarbamoyl-4-cyclopentylallophanimidate
methyl N-cyclopropylcarbamoyl-4-cyclopropylallophanimidate
methyl N-cyclopropylmethylcarbamoyl-4-cyclopropylmethylallophanimidate
methyl N-cyclohexylmethylcarbamoyl-4-cyclohexylmethylallophanimidate
methyl N-methylcarbamoyl-4-(2-cyclooctylethyl)allophanimidate
methyl N-(norborn-2-yl)carbamoyl-4-methylallophanimidate
methyl N-propargylcarbamoyl-4-propargylallophanimidate methyl N-isopropylcarbamoyl-4-(but-2-ynyl)allophanimidate
methyl N-isopropylcarbamoyl-4-methoxyallophanimidate
methyl N-(2-chloroethyl)carbamoyl-4-(2-chloroethyl)allophanimidate
methyl N-isopropylcarbamoyl-4-(1,2,2-trichloroethyl)allophanimidate
methyl N-methylcarbamoyl-4-(2-bromoethyl)allophanimidate
methyl N-tert-butylcarbamoyl-4-(2-iodoethyl)allophanimidate
methyl N-methylcarbamoyl-4-perfluoropropylallophanimidate
methyl N-isopropylcarbamoyl-4-trifluoromethylallophanimidate
methyl N-tert-butylcarbamoyl-4-fluoromethylallophanimidate
methyl N-methylcarbamoyl-4-(2-methoxyethyl)allophanimidate
methyl N-tert-butylcarbamoyl-4-ethoxymethylallophanimidate
methyl N-cyclohexylcarbamoyl-4-(2-methylthioethyl)allophanimidate
methyl N-ethylcarbamoyl-4-(2-ethylthioethyl)allophanimidate
methyl N-(2-cyanoethyl)carbamoyl-4-(2-cyanoethyl)allophanimidate
methyl N-benzylcarbamoyl-4-isopropylthioallophanimidate
methyl N-(p-methylbenzylcarbamoyl)-4-methylthioallophanimidate
methyl N-(p-chlorobenzylcarbamoyl)-4-tert-butylthioallophanimidate
methyl N-tert-butylcarbamoyl-4-methoxycarbonylmethylallophanimidate
methyl N-methylcarbamoyl-4-acetonylallophanimidate
methyl N-isopropylcarbamoyl-4-(2-chlorocyclohexyl)allophanimidate
methyl N-propylcarbamoyl-4-(3-bromocyclohexyl)allophanimidate
methyl N-isopropylcarbamoyl-4-(2-methylcyclohexyl)allophanimidate
methyl N-tert-butylcarbamoyl-4-(3,4-dimethylcyclopentyl)allophanimidate
methyl N-methylcarbamoyl-4-(4-butylcyclohexyl)allophanimidate
methyl N-tert-butylcarbamoyl-4-(2-ethylcyclopropyl)allophanimidate
methyl N-sec-butylcarbamoyl-4-sec-butylallophanimidate
methyl N-tert-butylcarbamoyl-4-isopropylallophanimidate, m.p. 97°–99° C
methyl N-methylcarbamoyl-4-isopropylallophanimidate, m.p. 85°–87° C
methyl N-methylcarbamoyl-4-sec-butylallophanimidate
methyl N-ethylcarbamoyl-4-isopropylallophanimidate, m.p. 66°–69° C
methyl N-methylcarbamoyl-4-cyclohexylallophanimidate
methyl N-methylcarbamoyl-4-phenylallophanimidate
methyl N-tert-butylcarbamoyl-4-sec-butylallophanimidate
methyl N-sec-butylcarbamoyl-4-isopropylallophanimidate, m.p. 66°–70° C
methyl N-methylcarbamoyl-4-tert-butylallophanimidate
methyl N-methylcarbamoyl-4-allylallophanimidate
methyl N-allylcarbamoyl-4-tert-butylallophanimidate
ethyl N-butylcarbamoyl-4-allylallophanimidate
ethyl N-butylcarbamoyl-4-tert-butylallophanimidate
ethyl N-butylcarbamoyl-4-cyclohexylallophanimidate
ethyl N-butylcarbamoyl-4-(p-bromophenyl)allophanimidate
methyl N-ethylthiocarbamoyl-4-tert-butylallophanimidate
methyl N-ethylthiocarbamoyl-4-phenylallophanimidate

EXAMPLE 6

To 5 parts of methyl 4-ethylthioallophanimidate (a compound of formula II) in 30 ml benzene was added 4.1 parts o-tolylisocyanate in 15 ml benzene. After stirring for 15 minutes at room temperature, the resulting solids were filtered off and recrystallized from benzene to give methyl N-ethylcarbamoyl-4-(o-tolyl)-thioallophanimidate (a compound of formula I), m.p. 152°–153° C.

Using the appropriate compound of formula II from the list below and the appropriate isocyanate, each compound of formula I listed below can be prepared similarly:

Compounds of Formula II methyl 4-methylthioallophanimidate
methyl 4-tert-butylthioallophanimidate
methyl 4-ethylthioallophanimidate
methyl 4-octylthioallophanimidate
methyl 4-isopropylthioallophanimidate
methyl 4-allylthioallophanimidate
methyl 4-butylthioallophanimidate
methyl 4-(2-cyclooctylethyl)thioallophanimidate
methyl 4-(norborn-2-yl)thioallophanimidate
methyl 4-propargylthioallophanimidate
methyl 4-(hex-3-ynyl)thioallophanimidate
methyl 4-propylthioallophanimidate
methyl 4-methoxythioallophanimidate
methyl 4-(2-chloroethyl)thioallophanimidate
methyl 4-(1,2,2-trichloroethyl)thioallophanimidate
methyl 4-(2-bromoethyl)thioallophanimidate
methyl 4-(2-iodoethyl)thioallophanimidate
methyl 4-perfluoropropylthioallophanimidate
methyl 4-trifluoromethylthioallophanimidate
methyl 4-fluoromethylthioallophanimidate
methyl 4-(2-methoxyethyl)thioallophanimidate
methyl 4-(ethoxymethylthioallophanimidate
methyl 4-(2-methylthioethyl)thioallophanimidate
methyl 4-(2-ethylthioethyl)thioallophanimidate
methyl 4-(2-cyanoethyl)thioallophanimidate
methyl 4-methoxycarbonylmethylthioallophanimidate
methyl 4-acetylthioallophanimidate
methyl 4-(2-chlorocyclohexyl)thioallophanimidate
methyl 4-(3-bromocyclohexyl)thioallophanimidate
methyl 4-(2-methylcyclohexyl)thioallophanimidate
methyl 4-(3,4-dimethylcyclopentyl)thioallophanimidate
methyl 4-(4-butylcyclohexyl)thioallophanimidate
methyl 4-(2-ethylcyclopropyl)thioallophanimidate
methyl 4-sec-butylthioallophanimidate
methyl 4-cyclohexylthioallophanimidate methyl 4-phenylthioallophanimidate
butyl 4-methylthioallophanimidate
butyl 4-allylthioallophanimidate
octyl 4-butylthioallophanimidate
ethyl 4-tert-butyl-1,3-dithioallophanimidate
methyl 4-allyl-1,3-dithioallophanimidate
methyl 4-isopropyl-1,3-dithioallophanimidate
methyl 4-tert-butyl-1,3-dithioallophanimidate
methyl 4-sec-butyl-1,3-dithioallophanimidate Compounds of Formula I methyl N-methylcarbamoyl-4-tert-butylthioallophanimidate, m.p. 132°–133° C
methyl N-tert-butylcarbamoyl-4-cyclohexylthioallophanimidate, m.p. 137°–144° C
methyl N-ethylcarbamoyl-4-allylthioallophanimidate
methyl N-octylcarbamoyl-4-methylthioallophanimidate
methyl N-octylcarbamoyl-4-propynylthioallophanimidate
methyl N-isopropylcarbamoyl-4-cyclohexylmethylthioallophanimidate, m.p. 123°–125° C
methyl N-allylcarbamoyl-4-phenylthioallophanimidate
methyl N-ethylcarbamoyl-4-(3,4-dichlorophenyl)thioallophanimidate
methyl N-butylcarbamoyl-4-(p-cyanophenyl)thioallophanimidate
methyl N-sec-butylcarbamoyl-4-isopropylthioallophanimidate, m.p. 104°–111° C
methyl N-methylcarbamoyl-4-(2-cyclooctylethyl)thioallophanimidate
methyl N-methylcarbamoyl-4-(norborn-2-yl)thioallophanimidate
methyl N-propargylcarbamoyl-4-propargylthioallophanimidate
methyl N-isopropylcarbamoyl-4-(4-ethylcyclohexyl)thioallophanimidate
methyl N-isopropylcarbamoyl-4-methoxythioallophanimidate
methyl N-(2-chloroethyl)carbamoyl-4-(2-chloroethyl)thioallophanimidate
methyl N-isopropylcarbamoyl-4-(1,2,2-trichloroethyl)thioallophanimidate
methyl N-methylcarbamoyl-4-(2-bromoethyl)thioallophanimidate
methyl N-tert-butylcarbamoyl-4-(2-iodoethyl)thioallophanimidate
methyl N-methylcarbamoyl-4-perfluoropropylthioallophanimidate
methyl N-isopropylcarbamoyl-4-trifluoromethylthioallophanimidate
methyl N-tert-butylcarbamoyl-4-fluoromethylthioallophanimidate
methyl N-methylcarbamoyl-4-(2-methoxyethyl)thioallophanimidate
methyl N-tert-butylcarbamoyl-4-ethoxymethylthioallophanimidate
methyl N-cyclohexylcarbamoyl-4-(2-methylthioethyl)-thioallophanimidate
methyl N-ethylcarbamoyl-4-(2-ethylthioethyl)thialophanimidate
methyl N-(2-cyanoethyl)carbamoyl-4-(2-cyanoethyl)thioallophanimidate
methyl N-tert-butylcarbamoyl-4-methoxycarbonylmethylthioallophanimidate
methyl N-methylcarbamoyl-4-(cyclooct-2-enyl)thioallophanimidate
methyl N-isopropylcarbamoyl-4-(2-chlorocyclohexyl)thioallophanimidate
methyl N-propylcarbamoyl-4-(3,4,4-trichlorocyclohexy)thioallophanimidate
methyl N-isopropylcarbamoyl-4-(2-methylcyclohexyl)thioallophanimidate
methyl N-tert-butylcarbamoyl-4-(3,4-dimethylcyclopentyl)thioallophanimidate
methyl N-isopropylcarbamoyl-4-(4-butylcyclohexyl)thioallophanimidate
methyl N-tert-butylcarbamoyl-4-(2-ethylcyclopropyl)thioallophanimidate
methyl N-tert-butycarbamoyl-4-isopropylthioallophanimidate
methyl N-methylcarbamoyl-4-isopropylthioallophanimidate, $n_D^{20}$ 1.5431
methyl N-methylcarbamoyl-4-sec-butylthioallophanimidate, m.p. 120°–122° C.
methyl N-ethylcarbamoyl-4-isopropylthioallophanimidate
methyl N-methylcarbamoyl-4-cyclohexylthioallophanimidate, $n_D^{20}$ 1.5522
methyl N-methylcarbamoyl-4-phenylthioallophanimidate, $n_D^{20}$ 1.6049
methyl N-tert-butylcarbamoyl-4-sec-butylthioallophanimidate, m.p. 105°–111° C.
butyl N-methylcarbamoyl-4-methylthioallophanimidate
butyl N-allylcarbamoyl-4-tert-butylthioallophanimidate
butyl N-methylcarbamoyl-4-(m-chlorophenyl)thioallophanimidate
octyl N-butylcarbamoyl-4-allythioallophanimidate
octyl N-butylcarbamoyl-4-tert-butylthioallophanimidate
octyl N-butylcarbamoyl-4-(p-nitrophenyl)thioallophanimidate
ethyl N-tert-butylthiocarbamoyl-4-isopropylthioallophanimidate
methyl N-allylthiocarbamoyl 4-tert-butylthioallophanimidate
methyl N-isopropylthiocarbamoyl-4-methylthioallophanimidate
methyl N-isopropylthiocarbamoyl-4-isopropylthioallophanimidate
methyl N-tert-butylthiocarbamoyl-4-tert-butylthioallophanimidate
methyl N-sec-butylthiocarbamoyl-4-sec-butylthioallophanimidate
methyl N-methylcarbamoyl-4-(cyclopent-2-enyl)thioallophanimidate
methyl N-methylcarbamoyl-4-(hexahydro-4,7-methanoindenyl)thioallophanimidate
methyl N-methylcarbamoyl-4-(3,4-dibromophenyl)-thioallophanimidate
methyl N-methylcarbamoyl-4-(p-tolyl)thioallophanimidate
methyl N-ethylcarbamoyl-4(α,α-dimethylbenzyl)thioallophanimidate
methyl N-methylcarbamoyl-4-furfurylthioallophanimidate
methyl N-isopropylcarbamoyl-4-(but-2-enyl)thioallophanimidate

EXAMPLE 7

17.5 Parts methyl 4-isopropylthioallophanimidate (a compound of formula II) is dissolved in 150 parts methylenechloride. This solution is added dropwise to a stirred solution of 17.8 g N,N'-thiocarbonyldiimidazole in 150 parts methylene chloride. The temperature is maintained at 0° during the addition and for 18 hours thereafter. Still maintaining 0°, 9.3 parts aniline is added. After this addition the mixture is allowed to warm to room temperature for two hours. The reaction mixture is then washed with several portions of water, to remove the imidazole formed, dried with magnesium sulfate, and the solvent evaporated at room temperature under reduced pressure. The residue is a good grade of crude methyl N-isopropylcarbamoyl-4-phenyl-1,3-dithioallophanimidate (a compound of formula I).

By substituting the appropriate methyl 4-substituted thioallophanimidates for the methyl 4-isopropylthioallophanimidate and/or appropriate amine for the aniline, the following allophanimidates can be prepared similarly:

methyl N-tetramethylenecarbamoyl-4-phenyl-1,3-dithioallophanimidate
methyl N-tert-butylcarbamoyl-4-phenyl-1,3-dithioallophanimidate
methyl N-sec-butylcarbamoyl-4-phenyl-1,3-dithioallophanimidate
methyl N-diisopropylcarbamoyl-4-phenyl-1,3-dithioallophanimidate
methyl N-isopropylcarbamoyl-4-cyclohexyl-1,3-dithioallophanimidate
methyl N-ethylthiocarbamoyl-4-tert-butyl-1,3-dithioallophanimidate
methyl N-tert-butylthiocarbamoyl-4-phenyl-1,3-dithioallophanimidate
methyl N-cyclopropylcarbamoyl-4-phenyl-1,3-dithioallophanimidate
methyl N-isopropylthiocarbamoyl-4-isopropyl-1,3-dithioallophanimidate
methyl N-tert-butylthiocarbamoyl-4-tert-butyl-1,3-dithioallophanimidate
methyl N-tert-butylthiocarbamoyl-4-isopropyl-1,3-dithioallophanimidate

EXAMPLE 8

319 Parts of 2-methyl-2-thiopseudourea sulfate (salt of a compound of formula IX), 2300 parts of acetonitrile and 400 parts triethylamine are combined. 400 Parts isopropylisocyanate are added rapidly and the temperature comes to 35° C. The solvent is removed under reduced pressure two days later and the oil is dissolved in dichloromethane and washed with water. The organic layer is dried and evaporated to give a tan solid. The solid is recrystallized from dichloromethane: hexane to give 813 parts methyl N-isopropylcarbamoyl-4-isopropylthioallophanimidate (a compound of formula I), (m.p. 125°–127° C).

The corresponding isomer can be formed as follows: 25 Parts of the geometrical isomer of methyl N-isopropylcarbamoyl-4-isopropylthioallophanimidate is dissolved in 25 parts dimethylformamide and heated to 40° C. After one hour, 12 parts of water is added to give 21 parts white solid after drying (m.p. 125°–127° C.). The infrared spectrum is different from starting material.

By substituting different isocyanates for the isopropyl isocyanate in the above example, the following compounds of formula I are prepared:

methyl N-tert-butylcarbamoyl-4-tert-butylthioallophanimidate, m.p. 151°–153° C
methyl N-cyclohexylcarbamoyl-4-cyclohexylthioallophanimidate, m.p. 138°–140° C
methyl N-allylcarbamoyl-4-allylthioallophanimidate
methyl N-cyclopentylcarbamoyl-4-cyclopentylthioallophanimidate
methyl N-cyclopropylcarbamoyl-4-cyclopropylthioallophanimidate
methyl N-cyclopropylmethylcarbamoyl-4-cyclopropylmethylthioallophanimidate
methyl N-cyclohexylmethylcarbamoyl-4-cyclohexylmethylthioallophanimidate
methyl N-sec-butylcarbamoyl-4-sec-butylthioallophanimidate, m.p. 105°–108° C

EXAMPLE 9

To a solution of 119 parts pf 4-thiobiuret (a compound of formula X) in 400 parts of water, 400 parts of methanol and 80 parts of 50% aqueous sodium hydroxide are added within 10 minutes at 25° C, 142 parts of iodomethane. The reaction mass is then stirred at 25° C for 2 hours. Evaporation of the methanol and part of the water under vacuum gives crude methyl thioallophanimidate (a compound of formula II), which can be used without further purification for subsequent reactions.

A mixture of 13 parts of methyl thioallophanimidate 74 parts of methylene chloride and 6 parts of methylisocyanate is refluxed for 2 hours. After standing overnight at room temperature, the solution is evaporated under vacuum to give crude methyl N-carbamoyl-4-methylthioallophanimidate (a compound of formula I).

By using the appropriate reactants, the following additional illustrative compounds of formula I and II can be prepared similarly:

Compounds of Formula II ethyl thioallophanimidate
isopropyl thioallophanimidate
propyl thioallophanimidate
butyl thioallophanimidate
octyl thioallophanimidate Compounds of Formula I methyl N-carbamoyl-4-ethylthioallophanimidate
methyl N-carbamoyl-4-isopropylthioallophanimidate
methyl N-carbamoyl-4-tert-butylthioallophanimidate
ethyl N-carbamoyl-4-cyclohexylthioallophanimidate
isopropyl N-carbamoyl-4-allylthioallophanimidate
propyl N-carbamoyl-4-allylthioallophanimidate
butyl N-carbamoyl-4-tert-butylthioallophanimidate
octyl N-carbamoyl-4-methylthioallophanimidate
octyl N-carbamoyl-4-phenylthioallophanimidate
octyl N-carbamoyl-4-(3,4-dichlorophenyl)thioallophanimidate

EXAMPLE 10

5.4 Parts of dimethylcarbamoyl chloride is combined with 10 parts pyridine and stirred until the temperature returns to 25° C. 8.0 Parts methyl 4,4-dimethylthioallophanimidate (a compound of formula II), in 50 parts methylene chloride is added in one portion. The mixture is refluxed overnight, then cooled to give a white solid. The solid is removed and the organic layer is extracted with 200 parts water at pH 3, dried and evaporated to give 5 parts methyl N-dimethylcarbamoyl-4,4-dimethylthioallophanimidate (a compound of formula I), m.p. 115.5°–117.5° C.

By substituting dimethylthiocarbamoyl chloride for the dimethylcarbamoyl chloride and methyl, 4,4- dimethyl-1,3-dithioallophanimidate for the methyl 4,4methyl there can be obtained methyl N-dimethylthiocarbamoyl-4,4-dimethyl-1,3-dithioallophanimidate.

By using the appropriate compound of formula II from the list below, the compounds of formula I in the list below can be prepared similarly:

Compounds of Formula II methyl 4,4-diethylthioallophanimidate
methyl 4,4-tetramethylenethioallophanimidate
methyl 4,4-hexamethylenethioallophanimidate
methyl 4,4-ethylenethioallophanimidate
methyl 4,4-ethyleneoxyethylenethioallophanimidate
methyl 4-isopropyl-4-methylthioallophanimidate
methyl 4-butyl-4-methylthioallophanimidate
methyl 4-ethyl-4-methylthioallophanimidate
methyl 4-tert-butyl-4-methylthioallophanimidate
methyl 4,4-dimethylallophanimidate
methyl 4,4-diethylallophanimidate
methyl 4-isopropyl-4-methylallophanimidate
methyl 4-tert-butyl-4-methylallophanimidate
methyl 4,4-tetramethyleneallophanimidate
ethyl 4,4-dimethylthioallophanimidate
isopropyl 4,4-dimethylthioallophanimidate
tert-butyl 4,4-dimethylthioallophanimidate
benzyl 4,4-dimethylthioallophanimidate
methyl 4,4-dimethyl-1,3-dithioallophanimidate
methyl 4-phenyl-4-methyl-1,3-dithioallophanimidate
methyl 4,4-pentamethylene-1,3-dithioallophanimidate Compounds of Formula I methyl N-dimethylcarbamoyl-4,4-diethylthioallophanimidate
methyl N-dimethylcarbamoyl-4,4-tetramethylenethioallophanimidate
methyl N-dimethylcarbamoyl-4,4-hexamethylenethioallophanimidate
methyl N-dimethylcarbamoyl-4,4-ethylenethioallophanimidate
methyl N-dimethylcarbamoyl-4,4-ethyleneoxyethylenethioallophanimidate
methyl N-dimethylcarbamoyl-4-isopropyl-4-methylthioallophanimidate
methyl N-dimethylcarbamoyl-4-butyl-4-methylthioallophanimidate
methyl N-dimethylcarbamoyl-4-butyl-4-methylthioallophanimidate
methyl N-dimethylcarbamoyl-4-ethyl-4-methylthioallophanimidate
methyl N-dimethylcarbamoyl-4-tert-butyl-4-methylthioallophanimidate
methyl N-dimethylcarbamoyl-4,4-dimethylthioallophanimidate
methyl N-dimethylcarbamoyl-4,4-diethylallophanimidate
methyl N-dimethylcarbamoyl-4-isopropyl-4-methylallophanimidate
methyl N-dimethylcarbamoyl-4-tert-butyl-4-methylallophanimidate
methyl N-dimethylcarbamoyl-4,4-tetramethyleneallophanimidate
ethyl N-dimethylcarbamoyl-4,4-dimethylthioallophanimidate
isopropyl N-dimethylcarbamoyl-4,4-dimethylthioallophanimidate
tert-butyl N-dimethylcarbamoyl-4,4-dimethylthioallophanimidate
benzyl N-dimethylcarbamoyl-4,4-dimethylthioallophanimidate
methyl N-dimethylcarbamoyl-4,4-dimethyl-1,3-dithioallophanimidate
methyl N-dimethylthiocarbamoyl-4-phenyl-4-methylthioallophanimidate
methyl N-dimethylthiocarbamoyl-4,4-dimethylthioallophanimidate
methyl N-dimethylthiocarbamoyl-4,4-pentamethylenedithioallophanimidate

EXAMPLE 11

5.6 Parts of 2-methyl-2-thiopseudourea sulfate (salt of a compound of formula IX), is placed in 50 parts water and cooled to 5° C. 4.5 Parts of methyl chlorothioformate is added in one portion followed by 4.8 parts of 50% sodium hydroxide added dropwise. A solid forms and is collected after 30 minutes. The N-(1-amino-1-methylthiomethylene)thiolmethylcarbamate (a compound of formula XII), m.p. 75°–65° C, is dissolved in 40 parts of methylene chloride with 4.2 parts of tert-butylisocyanate and stirred overnight. The solvent is removed under reduced pressure to give a solid. This solid is recrystallized from chlorobutane:hexane (1:1) to give 6.2 parts of methyl 4-tert-butyl-N-methylthiolcarbonyl-1-thioallophanimidate (a compound of formula III), m.p. 105°–106° C.

7.9 Parts of methyl 4-tert-butyl-N-methylthiolcarbonyl-1-thioallophanimidate and 2.9 parts of morpholine are combined in 50 ml of methanol and stirred overnight. The solution is poured into 50 parts water and the resulting solid is collected. The solid is recrystallized from acetonitrile to give 2.4 parts of methyl N-tert-butylcarbamoyl-4,4-ethyleneoxyethylenethioallophanimidate (a compound of formula I), m.p. 143°–144° C.

By using the appropriate reactants, the following illustrative compounds of formulae I and III can be prepared similarly:

Compounds of Formula III methyl 4-isopropyl-N-methylthiolcarbonyl-1-thioallophanimidate
methyl 4-methyl-N-methylthiolcarbonyl-1-thioallophanimidate
methyl 4-sec-butyl-N-methylthiolcarbonyl-1-thioallophanimidate
methyl 4-phenyl-N-methylthiolcarbonyl-1-thioallophanimidate
methyl 4-benzyl-N-methylthiolcarbonyl-1-thioallophanimidate
methyl 4-ethyl-N-methylthiolcarbonyl-1-thioallophanimidate
methyl 4-isopropyl-N-methylthiolcarbonyl-1,3-dithioallophanimidate
methyl 4-methyl-N-methylthiolcarbonyl-1,3-dithioallophanimidate
methyl 4-phenyl-N-methylthiolcarbonyl-1,3-dithioallophanimidate
methyl 4-tert-butyl-N-methylthiolcarbonyl-1,3-dithioallophanimidate Compounds of Formula I methyl N-isopropylcarbamoyl-4,4-dimethylthioallophanimidate
methyl N-ethylcarbamoyl-4,4-tetramethylenethioallophanimidate, m.p. 101°–105° C methyl N-methylcarbamoyl-4,4-pentamethylenethioallophanimidate
methyl N-phenylcarbamoyl-4,4-bis(2-chloroethyl)-thioallophanimidate
methyl N-benzylcarbamoyl-4,4-dipropylthioallophanimidate
methyl N-tert-butylcarbamoyl-4,4-tetramethylenethioallophanimidate, m.p. 148°–150° C
methyl N-isopropylcarbamoyl-4,4-diethylthioallophanimidate, m.p. 67°–68° C
methyl N-isopropylthiocarbamoyl-4,4-dimethylthioallophanimidate
methyl N-isopropylthiocarbamoyl-4,4-tetramethylenethioallophanimidate
methyl N-phenylthiocarbamoyl-4,4-dipropylthioallophanimidate
methyl N-tert-butylthiocarbamoyl-4,4-tetramethylenethioallophanimidate

EXAMPLE 12

18.8 Parts of methyl 4-butyl-4-methylthioallophanimidate (a compound of formula II) is dissolved in 200 parts methylene chloride with 20 parts triethylamine. 11 Parts methyl chlorothioformate is added slowly dropwise and a solid forms. After 2 hours the solid is collected and the filtrate is evaporated to give methyl 4-butyl-4-methyl-N-methylthiolcarbonyl-1-thioallophanimidate (a compound of formula III). This product is dissolved in 50 parts methanol and 10.1 parts diisopropylamine is added in one portion. The mixture is stirred overnight, then poured into 50 parts water to give a solid. The solid is collected and recrystallized from acetonitrile to give a good yield of methyl N-butyl-N-methylcarbamoyl-4,4-diisopropylthioallophanimidate (a compound of formula I).

By using the appropriate compound of formula II and the appropriate amine, the following compounds of formula I can be prepared similarly:
methyl N-tetramethylenecarbamoyl-4,4-dimethylthioallophanimidate
methyl N-tetramethylenecarbamoyl-4,4-dibutylthioallophanimidate
methyl N-tetramethylenecarbamoyl-4,4-isopropyl-4-methylthioallophanimidate
methyl N-tetramethylenecarbamoyl-4,4-pentamethyleneallophanimidate
methyl N-tetramethylenecarbamoyl-4,4-bis(2-chloroethylamine)-thioallophanimidate
methyl N-tetramethylenecarbamoyl-4,4-diisopropylthioallophanimidate
methyl N-tetramethylenecarbamoyl-4,4-diethylthioallophanimidate

EXAMPLE 13

5.0 Parts of methyl N-tert-butylcarbamoyl-4,4-dimethylthioallophanimidate (a compound of formula I) is suspended in water and 1.5 parts 50% sodium hydroxide is added with stirring. After solution is obtained, the water is removed under reduced pressure to give methyl N-tert-butylcarbamoyl-4,4-dimethylthioallophanimidate, sodium salt.

By substituting the appropriate compounds of formula I and bases, the following salts can be prepared in similar manner:
methyl N-isopropylcarbamoyl-4-isopropylthioallophanimidate, potassium salt
methyl N-tert-butylcarbamoyl-4-isopropylthioallophanimidate, calcium salt
methyl N-methylcarbamoyl-4-isopropylthioallophanimidate, magnesium salt
methyl N-tert-butylcarbamoyl-4-tert-butylthioallophanimidate, thioallophanimidate, lithium salt
methyl N-tert-butylcarbamoyl-4-tert-butylthioallophanimidate, ammonium salt
methyl N-tert-butylcarbamoyl-4-tert-butylthioallophanimidate, cesium salt

EXAMPLE 14

A solution of 12.5 parts thiophosgene in 150 parts methylene chloride is prepared. This is cooled to, and maintained at, −10° C while a mixture of methyl 4,4-diethylthioallophanimidate (a compound of formula II) 18.9 parts, triethylamine 10 parts, and methylene chloride 150 parts, is added over a ½ hour period. After the addition is complete the mixture is stirred at −10° C for an additional hour. Isopropylamine, 12 parts, is added and the mixture is allowed to warm to room temperature and stirred 1 hour. The reaction mixture is then washed with an equal volume of ice water and the methylene chloride layer collected, dried with magnesium sulfate, and the solvent evaporated at room temperature under vacuum. The residue is a good grade of crude methyl N,N-diethylcarbamoyl-4-isopropyl-1,3-dithioallophanimidate.

I claim:
1. Compounds of the formula:

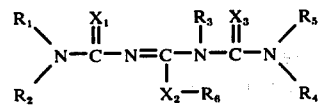

wherein:
$R_1$, $R_2$, $R_4$ and $R_5$ are each independently selected from the group consisting of hydrogen; alkyl of 1 through 8 carbon atoms; alkenyl of 3 through 4 carbon atoms; cycloalkyl of 3 through 8 carbon atoms; cycloalkenyl of 5 through 8 carbon atoms; cycloalkylalkyl of 4 through 10 carbon atoms; bicycloalkyl of 7 through 10 carbon atoms; hydrocarbyl arylalkyl of 5 through 9 carbon atoms; alkynyl of 3 through 4 carbon atoms; methoxy; phenyl; the above alkyl and alkenyl groups substituted with 1 through 3 chlorines, bromine, iodine, 1 through 7 fluorines, methoxy, ethoxy, methylthio, ethylthio, cyano, or acetyl; the above cycloalkyl and bicycloalkyl groups substituted with 1 through 3 chlorines, bromine, 1 or 2 methyls, or alkyl of 2 through 4 carbon atoms; phenyl substituted with 1 or 2 chlorines, 1 or 2 bromines, fluorine, nitro, cyano, alkyl of 1 through 4 carbon atoms, methoxy, or trifluoromethyl; and the above hydrocarbyl arylalkyl groups substituted with 1 chlorine or 1 methyl;
$R_3$ is hydrogen; alkyl of 1 through 4 carbon atoms; alkynyl of 3 through 4 carbon atoms; or alkenyl of 3 through 4 carbon atoms;
$R_6$ is alkyl of 1 through 8 carbon atoms; cycloalkyl of 5 through 8 carbon atoms; alkenyl of 3 through 8 carbon atoms; phenyl; or benzyl; and
$X_1$, $X_2$, and $X_3$ are each independently selected from oxygen and sulfur;
provided that:
a. at least one of $R_1$, $R_2$, $R_4$ and $R_5$ is other than hydrogen;

b. no more than one of $R_1$, $R_2$, $R_4$ and $R_5$ is phenyl, substituted phenyl; hydrocarbyl arylalkyl or substituted hydrocarbyl arylalkyl;

c. the total number of carbon atoms in $R_1$ and $R_2$ does not exceed 10;

d. the total number of carbon atoms in $R_4$ and $R_5$ does not exceed 10;

e. $R_1$ and $R_2$ are not both methoxy;

f. $R_4$ and $R_5$ are not both methoxy;

g. when $R_6$ is normal alkyl of 3 through 8 carbon atoms, cycloalkyl of 6 through 8 carbon atoms and benzyl, and $R_3$ is hydrogen, and one of $R_1$, $R_2$, $R_4$ and $R_5$ is phenyl, then only one of the other $R_1$, $R_2$, $R_4$ and $R_5$ can be other than hydrogen; and h. when one of $R_1$, $R_2$, $R_4$ and $R_5$ is 2,5-dichlorophenyl and $R_3$ is hydrogen, then only one of the other $R_1$, $R_2$, $R_4$ and $R_5$ can be other than hydrogen;

and the alkali metal, alkaline earth and ammonium salts of the above compounds in which $R_3$ is hydrogen.

2. The compounds of claim 1 where $R_1$ is hydrogen, alkyl of 1 through 6 carbon atoms, or alkenyl of 3 through 4 carbon atoms;

$R_2$ is alkyl of 1 through 4 carbon atoms or alkenyl of 3 through 4 carbon atoms, provided that the total number of carbon atoms in $R_1$ and $R_2$ does not exceed 8;

$R_3$ is hydrogen;

$R_4$ is alkyl of 1 through 6 carbon atoms, alkenyl of 3 through 4 carbon atoms or cycloalkyl of 5 through 6 carbon atoms;

$R_5$ is hydrogen, alkyl of 1 through 6 carbon atoms, cycloalkyl of 5 through 6 carbon atoms, benzyl, or alkenyl of 3 through 4 carbon atoms;

$R_6$ is methyl, ethyl, isopropyl or allyl;

$X_1$ and $X_3$ are oxygen; and $X_2$ is oxygen or sulfur.

3. The compound of claim 1 wherein $R_1$ is hydrogen or methyl;

$R_2$ is alkyl of 1 through 4 carbon atoms;

$R_3$ is hydrogen;

$R_4$ is alkyl of 1 through 4 carbon atoms, allyl or cycloalkyl of 5 through 6 carbon atoms;

$R_5$ is hydrogen;

$R_6$ is methyl;

$X_1$ is $X_3$ are oxygen; and $X_2$ is sulfur.

4. The compound of claim 1 which is methyl N-dimethylcarbamoyl-4-allylthioallophanimidate.

5. The compound of claim 1 which is methyl N-dimethylcarbamoyl-4-isopropylthioallophanimidate.

6. The compound of claim 1 which is methyl N-dimethylcarbamoyl-4-tert-butylthioallophanimidate.

7. The compound of claim 1 which is methyl N-dimethylcarbamoyl-4-cyclohexylthioallophanimidate.

8. The compound of claim 1 which is methyl N-dimethylcarbamoyl-4-(3,4-dichlorophenyl)thioallophanimidate.

9. The compound of claim 1 which is methyl N-tert-butylcarbamoyl-4-methylthioallophanimidate.

10. The compound of claim 1 which is methyl N-butylcarbamoyl-4-butylthioallophanimidate.

11. The compound of claim 1 which is methyl N-isopropylcarbamoyl-4-isopropylthioallophanimidate.

12. The compound of claim 1 which is methyl N-isopropylcarbamoyl-4,4-diethylthioallophanimidate.

* * * * *